United States Patent [19]

McDonald

[11] Patent Number: 5,116,766
[45] Date of Patent: May 26, 1992

US005116766A

[54] IMMUNE COMPLEX ISOLATION

[75] Inventor: Thomas L. McDonald, Omaha, Nebr.

[73] Assignee: The Board of Regents of the University of Nebraska, Lincoln, Nebr.

[21] Appl. No.: 170,777

[22] Filed: Mar. 21, 1988

Related U.S. Application Data

[60] Division of Ser. No. 816,700, Jan. 9, 1986, which is a continuation-in-part of Ser. No. 441.060, Nov. 12, 1982, abandoned.

[51] Int. Cl.$^5$ ............... G01N 33/531; G01N 33/564
[52] U.S. Cl. ................... 436/506; 436/507; 436/509; 436/542; 530/413; 530/387.1; 530/389.3; 424/88
[58] Field of Search ............ 436/506, 507, 509, 542; 424/88; 530/473, 387

[56] References Cited

U.S. PATENT DOCUMENTS 4,279,995  7/1981  Ricci ................... 436/804

Primary Examiner—Christine Nucker
Attorney, Agent, or Firm—Vincent L. Carney

[57] ABSTRACT

To diagnose diseases in patients, a protein complex, RhC, is prepared from horse serum by precipitating a white powder from the serum at a pH of 5.5 and processing to remove lipids at a pH of 8.2 using Tris-HCl as the buffer. It includes two components associated together to provide a molecular weight of 280,000 and having characteristics of a rheumatoid factor and a Clq-like subcomponent of the complement. The protein complex is incubated with human serum or plasma and then precipitated by dialysis against a high pH buffer (0.05M Tris-HCl pH 8.2). When precipitated, it coprecipitates the immune complexes from the human blood serum without substantial monomeric immunoglobulin to quantitatively isolate immune complexes from serum. Immunological assays then determine how much immune complex and what kind were in the serum.

3 Claims, No Drawings

IMMUNE COMPLEX ISOLATION

REFERENCE TO RELATED APPLICATIONS

This application is a divisional application of U.S. patent application Ser. No. 816,700 for IMMUNE COMPLEX ISOLATION filed by Thomas Lee McDonald on Jan. 9, 1986, which is a continuation-in-part application of U.S. patent application Ser. No. 441,060 IMMUNE COMPLEX ISOLATION filed by Thomas L. McDonald on Nov. 12, 1982, and assigned to the same assignee as this application.

BACKGROUND OF THE INVENTION

This invention relates to immune complex isolation.

It is known to isolate circulating immune complexes from sera by contacting the sera with a component that binds to the immune complexes and may be removed with them. It has been proposed to isolate the circulating immune complexes for use in diagnosing diseases or detecting auto-immune disorders or for research purposes by correlating the appearance of certain circulating immune complexes and their levels with diseases or with other factors to be detected or identified.

In one prior art technique, immunoglobulin complexes are precipitated with polyethylene glycol. This technique has a disadvantage in that, under many circumstances, the amount of monomeric immunoglobulin precipitated is so large that determinations based on total precipitation of monomeric immunoglobulin and immune complexes are difficult because changes in the amount precipated are not sufficiently representative of the immune complexes present in the subject. Moreover, if the sample is plasma rather than serum, other precipitates further complicate the analysis.

In another prior art technique for isolating circulating immune complexes, the circulating immune complex is bound to bovine conglutenin through fixed C3 complement components. In still another technique, the circulating immune complex is bound to human Clq which have been immobilised in an affinity chromatographic column and then eluted with a diaminoalkyl compound. Moreover, the patent to Masson et al., U.S. Pat. No. 4,283,383, discloses obtaining the rheumatoid factor and a complement factor and using them separately after covalently bonding them to third materials.

These prior art techniques have several disadvantages such as: (1) they do not isolate a sufficient quantity of circulating immune complexes to enable an analysis of the antigen moiety; (2) they are not sufficiently specific; and (3) they are relatively expensive and difficult to use because they require specialized equipment.

SUMMARY OF THE INVENTION

Accordingly, it is an object of this invention to provide a novel reagent for precipitating immune complexes.

It is a further object of this invention to provide a novel technique for isolating circulating immune complexes from serum or plasma.

It is a still further object of the invention to provide a novel technique for diagnosing diseases.

It is a still further object of this invention to provide a novel method of screening sera to detect the presence of abnormalities.

It is a still further object of this invention to provide a novel method for separating immune complexes from monomeric immunoglobulin and other materials in sera;

It is a still further object of this invention to provide a novel technique for precipitating immune complexes without specialized equipment.

It is a still further object of the invention to provide a technique for detecting auto-immune disorders.

It is a still further object of the invention to provide a novel immunotherapy technique.

It is a still further object of the invention to provide a novel kit for detecting circulating immune complexes.

In accordance with the above and further objects of the invention, a reagent that is a derivative of animal sera is obtained. This reagent has the ability to bind complexed immunoglobulin without binding to monomeric immunoglobulin. It may be used to screen for abnormalities by isolating immune complexes without substantial monomeric immunoglobulin.

The reagent and circulating immune complexes bound to it are efficiently separated from other materials in sera or plasma. The immune complexes and reagent may be separated from each other after being removed from sera or plasma and relatively pure antigen obtained. The combined reagent and circulating immune complexes may be separated from blood serum by precipitation or by attachment of the circulating immune complexes to reagent that has been immobilized on a solid surface.

The reagent, RhC, co-precipitates the immune complexes from the blood serum when: (1) incubated with animal blood serum or plasma; and (2) precipitated by dialysizing against a high pH buffer. In the alternative, RhC may be immobilized on a solid surface and animal blood serum or plasma brought into intimate contact with it.

The existence of disease is indicated by the amount of immune complex isolated and specific diseases may be diagnosed by conventional analysis of the precipitate or immune complex attached to the immobilized reagent. The reagent is isolated from the animal sera by changing the ionic strength of the serum and adjusting the pH to a value between 5.0 and 6.5. In the preferred embodiment, the ionic strength and ionic content is changed by dilution to facilitate the formation of the reagent.

The reagent includes at least two components which are believed to attach to different regions of the Fc of the antibodies only when the antibodies have combined with antigen. The reagent can be caused to separate from sera after the reagent has bound to immune complexes, usually by precipitation or by affinity chromatography, under conditions that to not cause the monomeric immunoglobulin to separate with it. The one factor is believed to be a rheumatoid factor or a portion of a rheumatoid factor and the other factor is believed to be a complement component or a portion of a complement component and they are believed to bind to portions of the Fc region of different antibody complexes.

One of the components of the reagent is IgG and in the preferred embodiment, this component is equine IgG and is the major protein content of the reagent. At least one other component of the reagent is anodic and combined with the cathodic Ig. This other component or components appears to be a component of horse serum because of its origin and because it reacts with anti-normal horse serum, which can detect its presence.

Together these two components selectively isolate a much larger portion of the immune complex than of monomeric imunoglobulin. Under some circumstances, both broader spectrum of the immune complexes and a larger amount of each type of immune complex is isolated. It is believed that IgM and all subclasses of IgG are isolated. The reagent may be packaged for every application to assay samples.

In use, the reagent and a human or other animal sample are mixed, the immune complexes bind to the reagent and the combination of reagent and immune complex is separated from blood sera or plasma using characteristics of the reagent or combination of reagent and immune complex that differ from the characteristics of monomeric immunoglobulin under some circumstances. The immune complexes are then analyzed.

To isolate the immune complex in one embodiment, the reagent and sample are mixed and: (1) the ionic strength of the mixture is changed; and (2) the pH is adjusted to between pH 6.5 and pH 9.5. The ionic strength is adjusted by adjusting the salt concentration to 0.05M in the pH range of 6.5 to 9.5. The immune complex precipitates and the precipitate is subject to separation of reagent and complex. In another embodiment, the reagent is immobilized on a solid surface and brought into contact with the sample. The immune complex binds to the immobilized reagent and is separated from the complex with the solid support. The complexes may be correlated with known complexes to identify them, or the antibodies may be separated from the antigen and the separate antigen or antibodies used for identification or immunotherapy. An antibody may be developed and used subsequently to identify the antigen or modified antibodies may be formed and used for immunotherapy. Antibodies may also be used to locate specific antigens in the subject.

From the above description, it can be understood that the technique and reagent of this invention has several advantages such as: (1) the reagent is inexpensive and easy to use to quantitate immune complexes; (2) the technique enables a simple and inexpensive diagnostic possibility for diseases; (3) the reagent may be sold separately to laboratories who may perform the diagnosis at their laboratories without the use of expensive equipment; (4) the technique is specific and accurate in quantitative determination of immune complexes; (5) the reagent precipates or otherwise isolates sufficient quantities of immune complex for analysis; (6) the technique permits a relatively simple quantitative isolation of immune complexes from serum or plasma; and (7) the technique produces better results at a lower cost.

SPECIFIC DESCRIPTION

Broadly, a protein complex is provided including at least portions of a rheumatoid-like factor and a complement-like component. This protein complex is formed as a result of the chemical manipulations of animal serum and has the characteristics of attaching to immune complexes but not monomeric immunoglobulin.

At least 25 micrograms (ug) of reagent protein is used to assay one sample and each sample that is assayed has at least the immune complexes of 25 microliters (ul) of undiluted animal serum. For screening in diagnosis, less than 600 ug of reagent must be used for the equivalent of 100 ul of serum or plasma to be able to effectively distinguish normal from diseased subjects.

The words "equivalent serum" or "equivalent plasma" are used to take into account the common use of dilution or concentration of the sera or plasma. For example, the use of a fraction of a diluted sample such as one-third of a sample diluted by two volume of diluent, each volume of which is equal to the one-third volume of the sample may be reacted with one-third as much reagent. The dilution aids in obtaining a more accurate value in cases where there are substantial amounts of immune complex. For separating the antigen when screening is not a concern, less than 2,000 ug of reagent must be used for the equivalent serum or plasma to be able to effectively separate antigens.

A reagent including this protein complex may be frozen or powdered and packaged for application or immobilized on a solid surface. In one embodiment of assay requiring bulk mixing of the reagent with the sample, 2.5 milligrams of protein for each milliliter of solution is used to assay one human sample.

The reagent is isolated from animal sera by drawing off the sera and precipitating a powder containing the reagent. Precipitation is caused by removing salts from the sera and adjusting the pH to a value between 5.0 and 6.5. The precipitate is purified prior to use by removing a large amount of the lipids from it.

This soluable protein complex precipitates when dialyzed against a high pH buffer and surprisingly, if it is incubated with serum or plasma containing immune complexes, it co-precipitates them at a pH in the range of 6.5 to 9.5 under low ionic strength conditions. Various immunological assays can then determine what kinds and how much immune complexes were in the original material. The complexes may be used to diagnose certain disorders of the autoimmune system and certain diseases.

In this specification serum is considered the clear liquid which separates in the clotting of blood from the clot and the corpuscles. Plasma is considered the fluid portion of the blood in which the corpuscles are suspended.

The amount of precipitate of immune complexes is consistent for a sample amount of reagent and conditions of precipitation and thus can be used to screen for abnormalities in the animal from which the serum was extracted. It is not known if all of the immune complexes are isolated, but the amounts are sufficiently consistent to provide positive indications of disorders.

To study diseases of the autoimmune system or to diagnose diseases, the precipitate is analyzed and identified in accordance with the particular disease. For diagnostic or experimental work, the reagent is sold in kit form with instructions for precipitating the immune complexes from specific animals.

It is believed that the reagent is isolated from different animals has substantially the same composition, behaves the same and has a molecular weight of substantially 250,000 to 325,000. It has an anodic and cathodic component with characteristics similar to the rheumatoid factor and Clq complement when subjected to electrophoresis and its activity is affected by heat in a manner similar to these two components and does not bind substantially to monomeric immunoglobulin.

The reagent is obtained from animal sera by removing the salts and precipitating at approximately a pH of 5.5 and by purifying to remove the glycoprotein and lipids until less than 25 percent by weight of the reagent includes contaminants. For the purpose of this definition, contaiminants are proteins other than the reagent which bind to monomeric immunoglobulin. The reagent has a molecular weight of 250,000 to 325,000 in the case of a reagent purified from equine sera.

More specifically, pooled equine blood (Central Nebraska Packing, Inc., North Platte, Nebraska) is allowed to clot overnight at 4 degrees C (Centigrade) and the serum collected following 1,200 x g centrifugation. One liter volumes are frozen at −4 degrees C for storage.

The isolation procedure of the reagent is a modification of the isolation procedure previously described for equine Clq in McDonald, T.L. and Burger, D. Immunol. 37: 517, 1979, the disclosures of which are incorporated herein by reference. In this procedure, eight volumes of 0.02M acetate buffer, pH 5.5 are added to 500 ml of equine serum. The mixture remains undisturbed at 4 degrees C for 15 hours after which the supernatant is siphoned and discarded. The precipitate is washed twice with 5 volumes of acetate buffer and dissolved in 0.5M tris-HCl buffer, pH 8.2 containing 0.5M NaCl and 0.001 EDTA. This solution (approximately 1/10 of the original serum volume) is clarified at 78,000×g for two hours at 4 degrees C.

The clear fluid between the lipid layer and the precipitate is aspirated with a needle and syringe and dialized at room temperature against 0.05M Tris-HCl and 0.001M EDTA, pH 8.2. The resulting precipitate is collected by centrifugation at 1,200 × g for 15 minutes, washed twice with the dialyzing buffer and dissolved in 0.05M Tris-HCl with 0.001M EDTA and 0.5M NaCl at pH 8.2.

In the next purification step, 1 ml aliquots of the dissolved precipitate are applied on a 2.5×30 cm Sepharose 6B-Cl column (Pharmacia Chemical Co., Piscataway, N.J.) equilibrated with PBS. Descending flow (30 ml/hour) of solvents is applied by gravity and the eluates monitored at 254 nm to detect protein peaks. The solvents are 0.05M PBS pH 7.2 or 0.05M Tris-HCl containing 0.5M NcCl at 8.2 pH.

The reagent is concentrated by dialyzing the pooled activity peak against 0.05 M Tris-HCl, pH 8.2. The resultant precipitate is redissolved in 0.5M Tris HCl pH 8.2 with 0.25M NaCl, diluted to 2.5 mg protein/ml, aliquoted in 0.5-ml volumes and stored at minus 20 degrees C.

In use, to isolate immune complexes, the reagent binds immune complexes to form a soluble protein complex. This soluble protein complex precipitates when dialyzed against a high-pH buffer (0.05M Tris-HCl, pH 8.2) and, if it is incubated with serum containing immune complexes, it co-precipitates them. Various immunological assays can then easily determine what kinds and how much immune complexes were in the original material. The antigens may be separated and used: (1) to identify diseases; and (2) in immunotherapy to sensitize leukocytes in vitro and thus to provide marked leukocytes to locate cancer cells or leukocytes to destroy cancer cells.

The reagent, because of unique properties, may be provided in a "kit" form for clinical use. The acutal composition of the kit depends upon circumstances of use but ideally contains all accessories such that the assay could be completed in even a modestly equipped clinic. Typically, for a powdered or frozen reagent, it may consist of: (1) 1 ml of RhC at 2.5 mg/ml, frozen or powdered which is enough for ten assays; (2) one vial of Tris-buffer salts to make 1 liter of dialyzing buffer a pH of 8.2; (3) ten dialysis bags (1 cm×5 cm: MW cutoff of 12-14,000); (4) ten snap-cap micro-fuge centrifuge tubes; (5) one vial ammonium acetate salts to make 10 ml of 0.3M final concentration; (6) one precut radial immunodiffusion plate; and (7) standard concentration of IgG for determination of standard curve.

It has been found that the reagent may be immobilized on solids such as plastics by ionic attraction without substantial loss of its biological activity. The generally used methods for such immobilization of proteins unexpectedly gave unsatisfactory results. For example, the common practice of immobilizing protein onto solid surfaces with either biocarbonate or phosphate buffers at a pH of 9.6 were not successful in immobilizing RhC in that the RhC did not retain its biological activity for the binding to immune complexes.

However, it was found that the use of TRIS (Tris 2-amino-2-hydroxymethyl-1,3-propanediol) buffer, provided satisfactory results. In the preferred embodiment, 0.05 Molar TRIS with 0.15 molar sodium chloride and 0.001 molar EDTA (ethylene-diamine-tetracetic acid) was used to successfully immobilize the reagent and maintain biological activity. Once the immune complex has been immobilized on a solid surface, standard techniques may be used for its analysis. Thus, the kit may include a solid surface rather than the powder, dialyzing supplies and centrifuge tubes.

These materials may be packaged together. Moreover, the quantities may in some kits be different and some parts may be omitted for certain applications. The package may be any enclosure capable of holding the parts within it for shipment.

To isolate the RhC reagent from horse serum, 8 volumes of 0.02M acetate buffer are added to one volume of serum at a pH 5.5, while stirring. The pH of the mixture is readjusted to 5.5 with glacial acetic acid and permitted to stand undisturbed overnight at 5 degrees C. The supernatent fluid including the serum is decanted and the precipitate centrifuged at 1,500×g for 10 minutes. The precipitate is washed two times in 0.02M acetate buffer, pH 5.5.

The precipitate is dissolved in 0.05M Tris-HCl pH 8.2 containing $10^{-3}$ ethylene-diamine-tetracetic acid (EDTA) and 0.5 M sodium chloride (NaCl). It is centrifuged at 78,000 x g for 2 hours at 5 degrees C and the clear fluid between the upper lipid layer and the precipitate is removed and dialyzed against 2 L of 0.05M Tris−HCl containing $10-3$ EDTA with no NaCl for a minimum of 4 hours at 5 degrees C.

The precipitate is: (1) concentrated by centrifugation at 1,500×g for 5 minutes and washed two times with dialyzing buffer; (2) dissolved in minimum volume of 0.05M Tris-HCl buffer, pH 8.2 containing $10-3$ M EDTA and 0.5M NaCl, at which point the volume is usually 1/25 starting volume of serum; and (3) separated by chromatograph on a 40 cm ×2.5 cm Sepharose 4B-Cl column equilibrated with dissolving buffer.

Equine RhC elutes in the second protein peak and is monitored at 254 nanometers. The entire second Sepharose 4B-Cl eluted peak is collected and dialyzed overnight at room temperature against 0.05M Tris-HCl buffer containing 0.001 M EDTA and no NaCl at pH 8.2.

The precipitate is concentrated by centrifugation at 1,500×g for 10 minutes and dissolved in minimum volume of 0.05M Tris-HCl containing 0.001M EDTA and 0.25M NaCl pH 8.2, which volume is usually 1/100 the original starting volume of serum. Each volume of RhC is clarified with 10 volumes of Frigen by vortexing the appropriate volumes at 15 second intervals for 2 minutes and centrifuging 10,000×g for 5 minutes. RhC is in the clear fluid layer at the top of the tube.

The clarified RhC is further purified by high pressure liquid chromatography (HPLC) in 0.5M Tris-phosphate buffer at a pH of 8.0 and concentrated by precipitating it with 0.05M Tris-HCl, pH 8.2. This precipitate is dissolved in minimum volumes of 0.05 M Tris HCl containing 0.001M EDTA and 0.25M NaCl pH 8.2.

The protein concentration of the purified equine RhC is determined and diluted to 2.5 milligrams/ml using the final dissolving buffer above. It is broken into aliquots and frozen at $-20$ degrees C. This purified RhC is used for the isolation of immune complexes from serum without further treatment.

To isolate the circulating immune complexes from serum, equal volumes of the serum of the animal and the reagent are mixed. A stock reagent has typically a concentration of two and one-half milligram of protein for each milliliter. A typical mixture may consist of 100 microliters of the sera taken directly from the animal and the 100 microliters of the reagent.

The mixture is placed in polystyrene tubes and incubated for 15 minutes at 37 degrees C and the contents are then dialyzed against two liters of 0.05M Tris-HCl at a pH of 8.2 for two hours. This process removes a substantial portion of the salts from the serum and the material is then centrifuged at 1,200 gravities for five minutes and the precipitate resuspended and washed twice in the dialyzing buffer.

The final precipitate is dissolved in 100 microliters of 0.05M Tris-HCl at a pH of 8.2 or 0.3M ammonium acetate at a pH 7.0. The solution is analyzed by rocket immunoelectrophoresis or radial immunodiffusion respectively.

The amount of immune complex which is isolated is indicative of disorder. It differs from species to species, but in humans, a range of between 12 to 15 micrograms of immune complex per milliliter of undiluted serum or plasma is normal. This is within accuracy of 5 micrograms. Variations from 12 to 15 microgram levels indicate a disorder.

To determine the accuracy of the tests, each sample is divided into 10 aliquots and each aliquot has the immune complex isolated. The measurements have a precision with a standard deviation of plus or minus 4 micrograms per milliliter.

The RhC factor in the immune complexes is separated by affinity chromatography by binding the immune complexes to staphylococcus protein-A (SPA) in the packing of the column or by HPLC. In the case of SPA, the immune complexes are then eluted by one of the following solvents, 0.1M glycine-HCl, pH 3.2, 1.0M sodium thiocyanate, pH 7.2 or 0.5M diiodosalicylic acid, pH 7.5 and the antigens separated by electrophoresis. The electrophoresis mobilities may be used to identify the antigen or the antigen may be separated for other analysis.

After separation, the antigens from the immune complexes can be analyzed for composition by a variety of techniques such as by high performance liquid chromatography or SDS (sodium dodecylsulfate) polyacrylamide gel electrophoresis (SDS-PAGE). AN antigen profile may be determined for certain particular diseases and used to identify a particular disease. Preparation of antibodies to common antigens of the disease can aid in detection and diagnosis and eliminate the interference of unrelated immune complexes or antigens.

A specific procedure for diagnosing diseases may include the steps of: (1) screening serum samples for presence of immune complex by the techniques described previously for RhC; (2) obtaining more serum from patients having large amounts of immune complexes; (3) separating immune complex from RhC by affinity chromatography (RhC does not bind) or HPLC; (4) separating the immune complexes into antigen and antibody components by electrophoresis; (5) analyzing antigens from the immune complexes for composition by one of a variety of known techniques such as high performance liquid chromatography or SDS-PAGE; (6) developing an "antigen profile" of circulating IC for each patient with the same disease; and (7) prepare antibodies to the "disease-common" antigen or antigens in the patients from the profile.

The antibodies may be used for diagnosis of the disease in other patients by detecting the antigen in the blood samples of the other patients. Moreover, marked antibodies may be prepared to locate antigens or leukocytes sensitized to destroy antigens in the subject.

The invention is illustrated by the following examples:

EXAMPLES

Preparation of the Reagent

In the preferred embodiment, equine RhC reagent is used although an RhC reagent with the same properties has been purified from the serum of other animals including human beings, rabbits and cattle. To prepare the reagent, eight volumes of 0.02 acetate buffer is added to one volume of horse serum at a pH 5.5 while stirring. The pH is readjusted to 5.5 with glacial acetic acid and permitted to stand undisturbed for several hours at 5 degrees C.

A precipitate is formed at this step; and it is believed that white precipitate obtains the reagent. The reagent has activity similar to that of a rheumatoid factor and a Clq complement component. The reagent is purified to remove other materials and specifically lipids as follows.

Firstly, the serum is decanted and the precipitate is centrifuged at 1,500×g for 10 minutes. It is then washed two times on 0.02M acetate buffer at a pH of 5.5.

Secondly, the precipitate is dissolved in 0.05M Tris-HCL (tris-hydrosy-methyl) amino methane with 0.05M hydrochloric acid added to adjust its pH to 8.2. The Tris-HCL contains 0.001M ethylene-diamine-tetracetic acid (EDTA) and 0.5M sodium chloride (NaC l). This solution will have approximately 1/10 of the original starting volume of the serum.

Thirdly, the resulting solution is centrifuged at 78,000 gravities for two hours at 5 degrees C. The clear fluid between the upper lipid layer and the precipitate is removed and dialyzed against two liters of 0.05M Tris-HCL containing 0.001M EDTA but with no sodium chloride for a minimum of four hours at 5 degrees C.

Fourthly, the precipitate from the previous step is concentrated by centrifugation at 1,500 gravities at five minutes and washed two times with the same dialyzing buffer used above.

Fifthly, the previpitate is dissolved in a minimum volume of 0.5M Tris-HCL buffer at a pH of 8.2 containing 0.001M EDTA and 0.5M sodium chloride. It is now usually at 1/25th of the starting volume of the serum.

Sixthly, the resulting solution is purified further on a liquid chromatograph using 40 centimeters by 2.5 centimeters Sepharose 4B-CL column equilibrated with 0.05M Tris-HCL buffer. Equine RhC elutes in the second protein peak monitored at 354 nanometers with a solvent of 0.05M Tris-HCL at a pH of 8.2 containing 0.001M EDTA and 0.5M sodium chloride. The solution forming the second protein peak is collected and dialyzed for several hours at room temperature against a 0.05M Tris-HCL buffer containing 0.001M EDTA but without sodium chloride. The buffer is maintained at a pH of substantially 8.2 to form a further purified white precipitate.

Seventhly, the precipitate is concentrated by centrifugation at 1.500 gravities for ten minutes and dissolve in a minimum volume of 0.05M Tris-HCl containing 0.001M EDTA and 0.25M sodium chloride at a pH of 8.2. At this point, the volume is approximately 1/100ths of the original starting volume of the serum.

Eighthly, more of the lipids are removed by taking each volume of RhC and clarifying it with 10 volumes of Frigen (1,1, 2-Trichlorotrifluroethane) by vortexing the appropriate volumes at 15-second intervals for two minutes and centrifuging at 10,000 gravities for five minutes. The RhC is in the clear fluid layer at the top of the tube and this clear fluid layer is removed from the foamed material created by the vortexing.

Finally, the clarified RhC is further purified by high-pressure liquid chromatography (HPLC) in 0.5M Tris-phosphate buffer, at a pH of 8.0 and concentrated by precipitating it with 0.05M Tris-CHl, pH 8.2. This precipitate is dissolved in minimum volumes of 0.05M Tris HCl containing 0.01M EDTA and 0.25M NaCl pH 8.2.

At this stage, the reagent is sufficiently pure and is prepared to an appropriate concentration. The protein concentration of the purified RhC is determined and diluted to 2.5 milligrams of RhC for each milliliter and 0.05M Tris-HCl containing 0.00M EDTA and 0.25M sodium chloride at a pH of 8.2. It may be broken into aliquots and frozen at a negative 20 degrees C. At this step, the reagent protein contains about 300 parts for every part of lipid or other contaminating material in the solution.

Preparation of Serum

To remove lipids, two ml of 1, 1, 2-Trichlorotrifluroethane (Frigen) is added to 0.25 ml of serum and mixed with vortex at 15 second intervals for total mixing time of 2 minutes. It is centrifuged at 1,500×g for 5 minutes and 0.1 ml of lipid-clarified serum is removed and placed in a clean glass tube.

Isolation of IC

To isolate immunoglobulin complexes, 0.1 ml of RhC reagent is added to each 0.1 ml of Frigen-Treated serum to be assayed for IC and the solution is incubated at 37 degrees C for 30 minutes.

The contents of each tube is removed and dialyzed against 1 liter of 0.05M Tris-HCl buffer containing 10-3M ethylene-diamine-tetra-acetic acid (EDTA) for two hours. The contents of each dialysis bag is removed with a pasteur pipette, and the bag is washed once with dialyzing buffer and centrifuged at 8,000×g for 5 minutes.

The supernatant is discarded and precipitate washed two times with dialyzing buffer. The precipitate is resuspended well by vigorously pipetting up and down with the bu bed-pasteur pipette.

The final precipitate is dissolved in 0.1 ml of 0.3M ammonium acetate (AA) pH 7.0.

Quantitation of IC

To determine the amount of immune complex, the isolated-IC is diluted 1:2 and 1:4 by adding 0.025 ml of sample to 0.025 ml of AA and 0.025 ml of sample to 0.075 ml of AA respectively.

Five microliters of each dilution and 5 microliters of solution of standard concentrations of IgG (10, 25, 40 and 60 micrograms/ml) are placed in wells of a radial immunodiffusion plate containing 0.2% of anti-IgG and incubated at room temperature for 18 hours.

The plate is soaked in distilled water for 1 hour, dried in warm air and stained.

INTERPRETATION

A standard curve is drawn by measuring the diameter of the diffusion rings obtained for the IgG standards and plotting these measurements against their respective concentration. The concentrations IgG in immune complexes of unknown samples is determined by measuring the diameter of the diffusion ring, interpreting from the standard curve and multiplying by the appropriate dilution.

Another method of assaying antibody contained in the RhC-isolated immune complexes is a modification of the rocket immunoelectrophoresis (RIEP) originally described in Laurell, C.B. (1972) Electroimmuno. assay, Scand. J. Clin. Invest. 29, 21, the disclosure of which is incorporated herein. This method is used for the quantitation of immunoglobulin classes and subclasses in both the original serum samples and the reagent precipitates.

Prior to gel casting, the appropriate antisera with specificity to the immunoglobulin (research Prod. Int., Elk Grove Village, Illinois) is diluted to 1 percent v/v final concentration in 56 degree C agarose (1 percent w/v in barbital buffer, pH 8.6). All serum samples are diluted 1:40 in 0.05M phosphate buffered saline at a pH 7.2 with undiluted immune complex isolates are incubated 30 minutes at 37 degrees C with an equal volume of 1 percent formaldehyde prior to RIEP. Five ul aliquots are then applied to 3 mm diameter wells, cut at the base of the gel slab, and immediately electrophoresed at 5 volts/cm gel for 4 hours at 4 degrees C.

Five ul samples of IgM, IgG1 and IgG2 (research Prod. Int., Elks Grove Village, Illinois) are used as standards at concentrations of 200, 100, 50 and 25 ug/ml. Following RIEP, the gel plates are dried and stained with 0.05 percent w/v Coomassie brilliant blue R-250 and destained with ETOH, $H_{20}$, glacial acetic acid (4.5: 4.5:1.0) as described by Laurell supra.

The reproducibility of the reagent in isolating CIC from infected and normal animals was evaluated by analysis of frozen aliquots of each pooled serum sample at three different times. The greatest standard error of the mean concentration of CIC in these triplicate serum samples is calculated. Analysis of individual samples, run in triplicate, is made to assess the reproducibility of the RIEP for analysis of CIC concentration, and the standard error is calculated.

The sensitivity of the RIEP was determined by electrophoresing various concentrations of each immunoglobulin classs or subclass against the appropriate homologous antisera-containing ge. The lowest detectable concentration is determined for all IgG subclasses.

EXAMPLE 1

LDV Infected Mice

Virus. Frozen LDV (lactic dehydrogenase virus) infected mouse serum was orignally obtained from Dr. D. Burger, Washington State University, Pullman, Washington, and use as seed virus. Stock virus preparations, titrations immunoglobulin classes and subclasses in both the original serum samples and the RhC precipitates. RESULTS The greatest standard error of the mean concentration of CIC in these triplicate serum samples was ±6 ug/ml (range ±2 ug to ±6 ug). Analysis of individual samples, run in triplicate in order to assess the reproducibility of the RIEP for analysis of CIC concentration, demonstrated a standard error of ±4 ug/ml.

The sensitivity of the RIEP was determined as described above, and the lowest detectable concentration was 5 ug/ml for IgM and 10 ug/ml for all IgG subclasses.

An indirect ELISA method was used to quantitate anti-LDV activity in the chronological serum samples obtained from LDV-infected mice. Diluted samples containing isolated CIC were incubated in ELISA wells that were previously coated with purified LDV antigen and the date scored for anti-LDV activity following addition of alkaline phosphatase-conjugated anti-mouse IgG as the ELISA second antibody as described above.

No anti-LDV activity was detected in any of the samples containing isolated CIC. This indicates that the LDV-specific antibody demonstrated in the isolated CIC by RIEP was bound to the LDV-antigen.

EXAMPLE 2

Diabetic Hamsters

IC were isolated from the serum of diabetic and normal hamsters by co-precipitation with the reagent, RHC as described in the general section.

Syrian hamsters at six weeks of age and approximately 100 g in weight were injected intraperitoneally, once each day for three days with 50 mg streptozotocin (SZ) per kg of body weight. Age-matched animals were similarly injected iwth acidified saline and were used as controls.

All hamsters had free access to water and lab chow, however, none of the animals received insulin. Serum samples were obtained from blood that was drawn from the orbital sinus of each hamster at weekly intervals. Serum glucose was determined with a Beckman II glucose analyzer. Only those animals with faster-glucose concentrations of greater than 300 mg/dl were considered to be diabetic. The serum was stored at −70 degrees C for future use in IC assays.

RESULTS

Immune complexes isolated from the serum of the Sz-induced diabetic hamsters by co-precipitation with RhC comprised an unknown antigen and IgG at two distinct time intervals during the 12-week chronological study. Although all diabetic hamsters with hyperglycemia of 300 mg/dl had IC, there was no correlation between the occurrence or concentration of IC and the degree of hyperglycemia.

The isolation of IC from diabetic and normal hamster serum by equine RhC was shown to be highly reproducible by analysis of frozen aliquots of the same serum sample at three different times. It has a coefficient of variations (CV) of 1.6 percent. Interexperimental variation in the RIEP analysis of triplicate samples was also highly reproducible (CV of 1.2 percent). The lowest detectable concentration of IgG by RIEP was 25 ug/ml and defined the lower limits of the test system.

EXAMPLE 3

In Vitro Anti-BSA and IgG

Anti-BSA was prepared by subcutaneous inoculation of 5 rabbits, each received 2 mg BSA dissolved in 1 ml of PBS - Freund's complete adjuvant and each was boosted three weeks later with the same BSA concentrations in Freund's incomplete adjuvant. Anti-BSA activity of these was determined by the highest titer at which a visible precipitation line was seen in an Ouchterlony-type gel diffusion system. Rabbit sera having an Ouchterlony titer of 16 or greater two weeks following booster inoculations were pooled and stored at −20 degrees C for IC preparation.

$^{125}$I-HG was prepared by pooling the non-aggregated protein peak eluted from a Sephadex G-200 column (Pharmacia Chemical Co., Piscataway, N. J.) loaded with 10 mg/ml 125I-labeled unheated Cohn Fraction II.

Radiolabeling of both human IgG and BSA was performed as described in Enzymobead radio-iodination reagent bulletin (Bio-Rad Laboratories, Richmond, Calif.). The labeled protein was exhaustively dialyzed at 4 degrees C against pH 7.2 PBS to remove unbound 125I.

IC were prepared in PBS by adding 125I-BSA and rabbit anti-BSA in the desired Ag-Ab ratios. The anti-BSA serum was diluted 1:4 and incubated with decreasing concentrations of 125I-BSA in order to determine Ag-excess, Ag-Ab equivalence, Ab excess and percent soluble IC.

AHG was prepared by heating 2.0 ml of a 20 mg/ml solution of 125I-Cohn Fraction II (Sigma Chemical Co., St. Louis, Missouri) at 63 degrees for 20 minutes. Insoluble aggregates were removed by 1,200×g centrifugation for 15 minutes and the supernatant applied to a 1.5×25 cm Sephadex G-200 column equilibrated with pBS. AHG that eluted in the void volume was pooled, aliquoted and frozed at −70 degrees C.

The ability of the RhC factor to co-precipitate bound as opposed to unbound IgG is demonstrated with $^{125}$I-labeled Cohn Fraction II in aggregated (AHG) and unaggregated (HG) states following the procedure above for isolating immune complexes.

To establish if the RhC factor was a limiting factor for the isolation of Ag-Ab complexes, it was necessary to determine the optimum concentration required to co-precipitate a predetermined amount of AHG. Radiolabeled AHG and HG were diluted to approximately 45 ug (micrograms) of protein contained in 100 ul (microliters) of PBS and was represented by approximately 2.22×105 cpm. To these 100 ul samples, 100 ul of RhC varying in protein concentration from 100 ug/ml to 1 mg/ml was added.

To determine the efficacy of the RhC factor to co-precipitate soluble Ag-Ab (antigen-antibody) complexes in Ag or Ab excess, the following in vitro BSA anti-BSA model system was used, using the above materials. In this series of experiments, the BSA anti-BSA model was defined with respect to Ag-Ab equivalence (maximum insoluble IC) and the percent soluble IC.

One-half ml of a 1:4 diultion of rabbit anti-BSA serum was incubated with an equal volume of two fold serial dilutions of 125I-BSA for one hour at 37 degrees C. Following 1,200×g centrifugation for 15 minutes, the percent of insoluble BSA-anti-BSA immune complexes was determined. In our system, Ag-Ab equivalence was reached at 64 ug/ml of 125I-BSA which precipitated approximately 93% of the available BSA antigen. The percent of soluble immune complexes represented by the total remaining in the 1 ml supernatants was calculated by (NH4)2SOv4 precipitation analysis on one-half of the sample volume. From a concentration range of 125 ug of BSA (2×antigen excess) to 8 ug BSA (8×antibody excess) approximately 85 percent of the 125I BSA in solution was a soluble IC. The remaining one-half (500 ul) of the 125I BSA anti-BSA supernatants was incubated with 500 ul of the RhC.

RESULTS

At Ag-Ab equivalence and all conditions of Ab excess, 100 percent of the soluble BSA-anti-BSA, IC was co-precipitated with the RhC factor. Under conditions of 2×Ag excess approximately 80 percent of the soluble IC were co-precipitated and minimal isolation could be obtained at Ag concentrations greater than 8×. Dialysis of these soluble IC-containing solutions without addition of RhC factor resulted in no precipitation of radioactivity. In addition, the RhC would not co-precipitate free 125I BSA that was not bound as an IC.

Heat-aggregated huma IgG (AHG) and monomeric human IgG (HG) were also subjected to IC-isolation by RhC. The percentage of labeled IgG that co-precipitated with the RhC following dialysis was calculated from the 125I-protein specific activity and the results are expressed in Table 1.

Increasing concentrations of RhC material did not affect the co-precipitate of HG. In control experiments, neither AHG or HG precipitated without the addition of the RhC. It was determined from these results that the RhC diluted to 2.5 mg/ml would be used with equal volumes of IC samples for maximum efficiency.

TABLE 1

Comparison of $^{125}$I Unaggregated and Heat Aggregated IgG Co-Precipitated with RhC

| Sample[a] | Unbound IgG cpm | Bound IgG cpm | Percent Co-Precipitated |
|---|---|---|---|
| Unaggregated IgG | 116,974 ± 1,636 | 887 ± 23 | 0.8% ± 0.3% |
| Heat Aggregated IgG | 806 ± 64 | 69,530 ± 650 | 99% ± 0.5% |

[a] Samples of $^{125}$I human IgG were diluted to approximately 105 cmp/100 ul and incubated with RhC factor as described earlier. The IgG not bound vs. bound was reflected by the cpm remaining in the supernatant following dialysis vs. the cpm/co-precipitated respectively.
[b] ± standard deviation

SUMMARY

The RhC reagent co-precipitated 99 percent of the 125I-labeled aggregated human IgG (AHG) following dialysis against 0.05M Tris-Hcl, pH 8.1 compared to only 0.8 percent of the unaggregated human IgG (HG). When incubated with bovine serum albumin (BSA) anti-BSA soluble immune complexes (IC) prepared at antigent (Ag)-antibody Ab equivalence of in Ab excess, the RhC co-precipitated 100 percent of the available complexes. Under conditions of 2x Ag excess, RhC was less efficient as demonstrated by co-precipitation of 80 percent of the available IC.

EXAMPLE 4

Human—No Known Disease

Serum from patients clinically normal was processed by the isolation of immune complex procedure in the general section and reproducibility was checked by the procedure in the general section above.

RESULTS

The level of immune complexes isolated for all 25 patients fell within the range of 12–18 micrograms with the mean amount being 15 micrograms to provide a standard error of 5 micrograms.

EXAMPLE 5

Humans—Diabetics With Late Complications

Serum from 36 patients who had been diagnosed as having diabetes with late complications was obtained and the immune complexes separated from it as described under Isolation of Immune Complexes above. The reproducibility of the measurements was tested as described in the section under reproducibility by rocket immunoelectrophoresis or radio immunodiffusion.

RESULTS

Of the 36 patients clinically diagnosed as having diabetes, 34 showed an elevated level of immune complexes. The total rante was from a normal range of 15 micrograms to 144 micrograms. The standard deviation on the repeated samples was plur or minus 6 micrograms.

EXAMPLE 6

Human—Streptococcus Infected Patients

Serum from 37 patients who had been clinically diagnosed as having streptococcus infection was drawn and the immune complexes separated in the manner described in the general section of the examples. The reproducibility was checked by the procedure described in the general section.

RESULTS

The level of the immune complexes of 22 of the 37 samples was elevated above normal. The range of immune complexes was from 14 micrograms to 280 micrograms with a standard deviation on repeated samples of plus or minus 5 micrograms.

EXAMPLE 7

Human—Streptococcus Infected Patients With Bacteremia

Serum from six patients clinically diagnosed as being infected with streptococcus with bacteremia was obtained and the immune complexes isolated in accordance with the procedure in the general section. The reproducibility was checked in accordance with the procedure under Reproducibility in the general section.

RESULTS

Six of the six patients had immune complexes above a normal level. The range of immune complexes was 140 micorgrams to 260 micrograms with a standard deviation on repeated samples of plus or minus 6 micrograms.

EXAMPLE 8

Human—Juvenile Rheumatoid Arthritis (Active Disease)

Serum was obtained from two patients diagnosed as having juvenile rheumatoid arthritis in an active stage and immune complexes were isolated following the procedure in the general section of these examples. The reproducibility was tested as stated in the general section.

RESULTS

Both of the samples showed elevated levels of immune complexes, with both of them showing 240 micrograms.

EXAMPLE 9

Human—Juvenile Rheumatoid Arthritis (Remission)

Serum was obtained from two patients diagnosed as having had juvenile rheumatoid arthritis which was in remission. The immune complexes were isolated as described in the general section of these examples.

REMARKS

Neither of the patients showed elevated levels of immune complexes as compared to the levels of Example 5 for clinical diagnosis of normal patients. The levels were between 12 and 15 micrograms.

EXAMPLE 10

HUMAN—JUVENILE—ACUTE NEPHRITIS

Samples of serum were obtained from three patients clinically diagnosed as having acute nephritis. The samples were processed for the isolation of immune complexes using the procedure described in the general section of these examples.

RESULTS

All three of the patients showed elevated levels of immune complexes within the range of 90 micrograms to 120 micrograms.

EXAMPLE 11

Human—Juvenile—Bacterial Endocarditis

Samples were obtained from two patients clinically diagnosed as having bacterial endocarditis and the immune complexes were isolated using the procedure provided in the general section of these examples.

RESULTS

Both patients showed elevated immune complexes within the range of 140 micrograms to 180 micrograms.

EXAMPLE 12

Rats—Comparison of Precipitating Techniques

Immune complexes were isolated from the serum of rats with streptozotocin-induced diabetes. One method using RhC as described in the general section and the other using an affinity chromatography with human polyclonal rheumatoid factor being attached to the packing. Both methods precipitated immunoglobulin but the affinity chromatography method isolated both bound and monomeric immunoglobulin whereas the method described in this section precipitated only quantities of immune complexes without monomeric immunoglobulin.

EXAMPLE 13

Growth of Tumors in Mice

Samples of serus were obtained from twenty mice without tumors and the immune complexes isolated using the procedure described in the general section of these examples. The immune complexes were not elevated. Twenty mice with bladder tumors had samples drawn from them at periods of one week, two weeks and three weeks.

In the fourth week, the tumor was removed from ten animals and the immune complexes measured from serum in four weeks for both the ten animals with the tumor removed and the ten animals in which the tumor remained. All ten animals with tumors died between the fourth and fifth week. It was noted that the primary tumor had metastisized to the lungs.

Serum was drawn from animals with the tumor removed at the fifth week. The immune complexes were isolated using the procedures in the general section and the reporducibility was measured using the procedures in the general section of these examples.

RESULTS

The mice without tumors showed no elevation of immune complexes. The animals with tumors showed a mean value of immune complex of 55 micrograms with a standard deviation of plus or minus 8 micrograms in the first week, a precipitation of immune complexes of 80 micrograms with a standard deviation of 5 micrograms in the second week, a level of immune complexes isolated of 170 micrograms with a standard deviation of plus or minus 6 micrograms in the third week.

In the ten animals for which the tumor was removed in the fourth week, the average of the immune complexes was 25 micrograms with a standard deviation of plus or minus 6 micrograms; and in the tumored animals it was 180 micrograms with a standard deviation of 5 micrograms. Of the animals with the tumor removed, in the fifth week, was 80 micrograms with a standard deviation of plus or minus 5 micrograms.

From the above description, it can be understood that the technique and reagent of this invention has several advantages such as: (1) the reagent is inexpensive and easy to use to quantitate immune complexes; (2) the technique enables a simple and inexpensive diagnostic possibility for disease; (3) the reagent may be sold separately to laboratories who may perform the diagnosis at their laboratories without the use of expensive equipment; (4) the technique is specific and accurate in quantitative determination of immune complexes; (5) the reagent precipitates sufficient quantities of immune complex for analysis; (6) the technique permits a relatively simple quantitative isolation of immune complexes from serum; and (7) the technique produces better results at a lower cost.

Although a preferred embodiment has been described with some particularity, many modifications and variations may be made in the preferred embodiment without deviating from the invention. Accordingly, it is to be understood that, within the scope of the appended claims, the invention may be practiced other than as specifically described.

What is claimed is:

1. A method comprising the steps of:
   obtaining sera from a mammal;

removing salts and adjusting the pH of the sera to form a precipitate at a pH of between 5.0 and 6.5;

purifying the precipitate by removing glyco-proteins until the reagent has less than 25 percent by weight of proteins whereby a reagent is obtained having properties of combining with the FC region of complexed antibodies without binding to monomeric immunoglobulin;

mixing at least 25 micrograms of the reagent with a sample of serum from the subject at a pH in the range of 6.5 to 9.5, whereby the reagent binds to the immune complex;

separating the bound immune complexes as a precipitate from the sera;

separating the reagent from the immune complex by chromatography;

separating the antigen and the antibody of the immune complex by electrophoresis; and developing an antiserum or monoclonal antibody against the antigen(s) to detect antigen in patients that have specific disorders.

2. A method comprising the steps of:

bringing each of a plurality of samples of fluids from different animals which fluids include complexed immunoglobulin into contact with a sufficient amount of a protein complex having a rheumatoid-like factor and a complement-like factor to separate the immune complexes wherein the protein complex selectively binds to immune complexes in the plurality of samples without binding to monomeric immunoglobulin, and wherein the samples of fluid are brought into contact with the protein complex while the protein complex is bound to a solid support and the immune complexes are separated from the support; and selecting those animals with an amount of immunoglobulin complex precipitated which is at least about fifteen percent larger than the precipitate from animals known to have no diseases for further diagnosis.

3. A method comprising the steps of:

contacting an adequate proportion of fluid from an animal having immune complexes with a solid support to which is bound a protein complex having a rheumatoid-like factor and a complement-like factor to separate the immune complexes, wherein the protein complex selectively binds to immune complexes without binding to monomeric immunoglobulin;

separating the immune complexes and the protein complex from the animal fluids after they have been bound together whereby immune complexes are isolated;

separating the antigen from the antibody in the immune complexes; and developing at least one of an antiserum and a monoclonal antibody against a corresponding one of the antigen(s), and antibodoies and using it to diagnose patients that have specific disorders.

* * * * *